United States Patent [19]

Lazarow et al.

[11] Patent Number: 4,709,703
[45] Date of Patent: Dec. 1, 1987

[54] IMAGING SYSTEM AND METHOD USING RADIOPAQUE MICROSPHERES FOR EVALUATION OF ORGAN TISSUE PERFUSION

[75] Inventors: Normand H. Lazarow; Alfred A. Bove, both of Rochester, Minn.

[73] Assignee: Mayo Foundation, Rochester, Minn.

[21] Appl. No.: 796,952

[22] Filed: Nov. 12, 1985

[51] Int. Cl.⁴ .......................... A61B 6/00; A61B 5/02
[52] U.S. Cl. .................................. 128/654; 128/695; 424/4
[58] Field of Search ........................ 424/1.1, 18–38, 424/4; 128/1.3, 661, 663, 653–658; 604/890; 427/213.3; 264/4.6, 4, 4.1, 4.4, 4.7; 252/62.53, 62.54, 62.55; 260/399

[56] References Cited

U.S. PATENT DOCUMENTS

| | | | |
|---|---|---|---|
| 4,331,654 | 5/1982 | Morris | 424/38 |
| 4,364,392 | 12/1982 | Strother et al. | 128/325 |
| 4,452,773 | 6/1984 | Molday | 424/1.1 |
| 4,492,720 | 1/1985 | Mosier | 427/213.3 |
| 4,572,203 | 2/1986 | Feinstein | 128/661 |
| 4,594,193 | 6/1986 | Regen | 260/399 |
| 4,619,913 | 10/1986 | Luck et al. | 424/19 |

Primary Examiner—Donald P. Walsh
Assistant Examiner—T. J. Wallen
Attorney, Agent, or Firm—Merchant, Gould, Smith, Edell, Welter & Schmidt

[57] ABSTRACT

A radiologic imaging system and method (20) using radiopaque microspheres for evaluating organ tissue perfusion. Radiopaque microspheres are administered to organ tissue (22) which is then scanned using a computerized tomography (CT) scanner (24) which provides a visual CT image (26) and/or statistical report (28) providing an indication and/or measurement of organ tissue perfusion.

16 Claims, 3 Drawing Figures

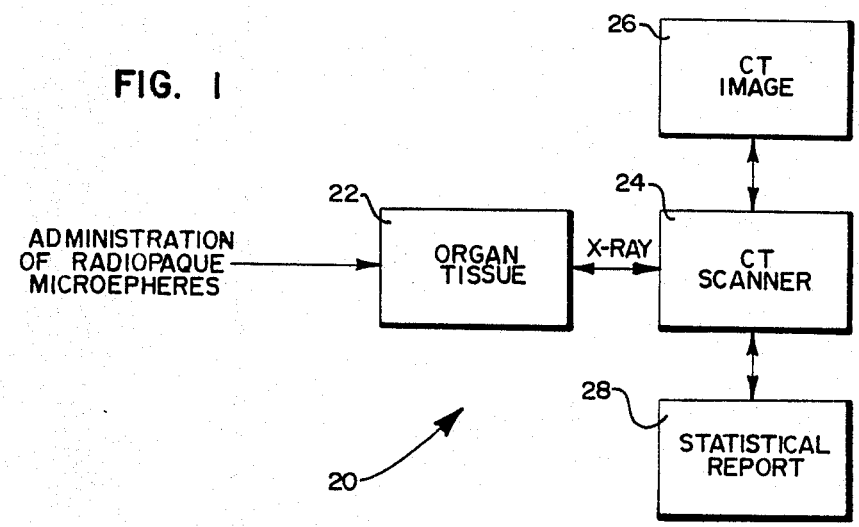
FIG. 1
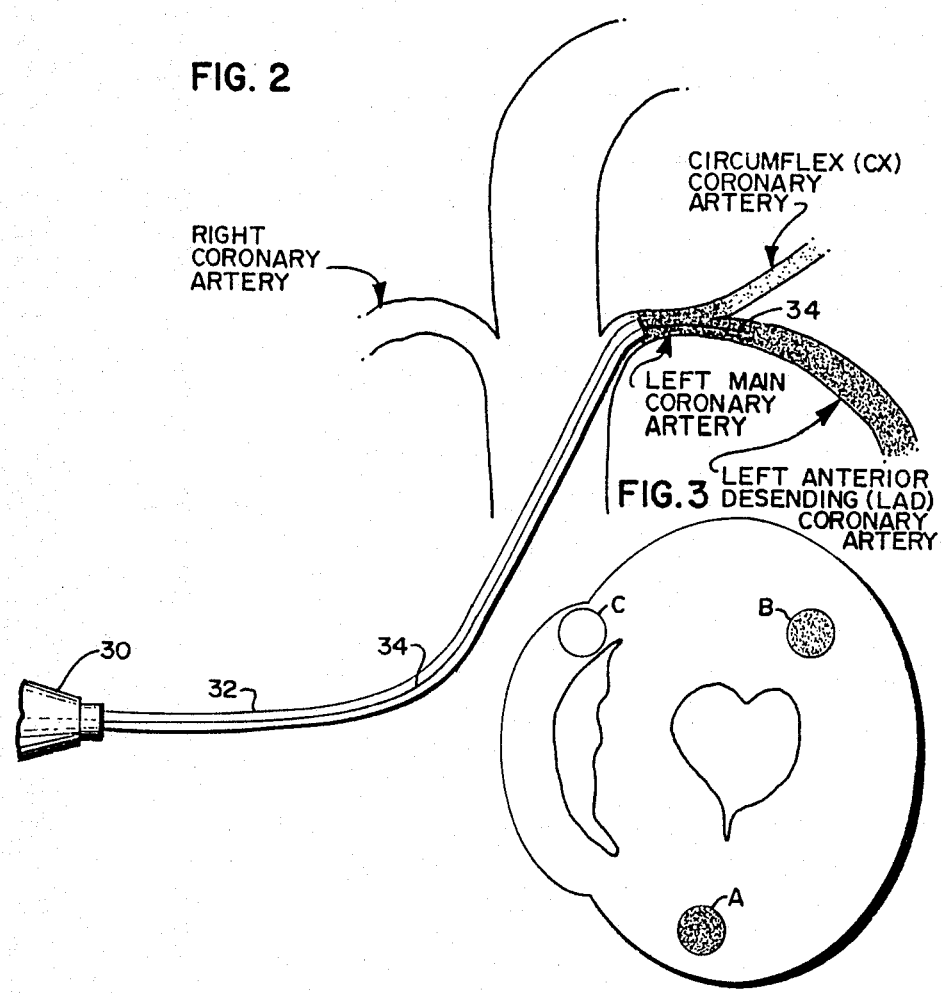
FIG. 2
FIG. 3

IMAGING SYSTEM AND METHOD USING RADIOPAQUE MICROSPHERES FOR EVALUATION OF ORGAN TISSUE PERFUSION

BACKGROUND OF THE INVENTION

The present invention relates to an imaging system and method. More particularly, the present invention relates to an imaging system and method using radiopaque microspheres to evaluate organ tissue perfusion.

The present standard for measuring organ tissue perfusion/flow in animal studies is the "radioactive" microsphere technique wherein radioactive microspheres are administered to the organ tissue. A significant limitation with this technique, however, is that it requires organ dissection and postmortem radioactive counting for flow determination. Moreover, this technique is limited to animal studies and cannot be used in the clinical evaluation of humans.

Measurements of organ tissue perfusion in both animals and humans has been obtained with computerized tomography (CT) imaging in conjunction with a soluble contrast agent such as a water soluble iodinated contrast agent. However, problems associated with this technique include the recirculation of the contrast agent and its partial diffusion into the tissue. As a result, curve fitting techniques such as a gamma variant analysis are required and dynamic "fast" CT scanning is necessary to accurately image the contrast agent bolus.

The present invention solves these and many other problems associated with the prior art.

SUMMARY OF THE INVENTION

The present invention relates to an imaging system and method using radiopaque microspheres for evaluation of organ tissue perfusion.

An advantage of the present invention is that organ tissue perfused with radiopaque microspheres can be adequately visualized with computerized tomography (CT) and can be distinguished from nonmicrosphere perfused tissue. Moreover, organ tissue perfusion can be quantified by the CT number of detected radiopaque microspheres in a given region of interest.

Yet another advantage is that the radiopaque microspheres occlude terminal capillary beds, whereby both the recirculation and partial tissue diffusion problems attendant with the use of a soluble contrast agent are avoided. Accordingly, CT scanning does not have to be performed immediately after administration of the contrast agent. Additionally, dynamic "fast" CT scanning with following of the contrast agent bolus in the intravascular compartment and curve fitting techniques are not necessary.

Another advantage of the present invention is that it can be used to evaluate organ tissue perfusion/blood flow in virtually any organ.

Still another advantage is that the radiopaque microspheres can be selectively administered to a specific organ via well-known conventional peripheral arterial catherization techniques or can be systemically distributed throughout the body by administering radiopaque microspheres through a left atrial cardiac injection.

Another advantage of the present invention is that it provides for an accurate quantitive measurement of blood flow through and throughout any particular organ and the quantitive measurement of blood disbursement throughout the body.

Still another advantage of the present invention is that the administration of radiopaque microspheres in doses necessary to enable visualization with CT do not alter or interfere with organ tissue perfusion parameters.

The present invention preferably uses nonradioactive radiopaque microspheres or microspheres having such a low level of radioactivity so as to not be deleterious to the organ tissue and/or the organsism. Moreover, the tissue need not be dissected postmortem, as is the case when radioactive microspheres are used and radioactive counting is performed. Accordingly, the present invention provides for a non-invasive assessment of organ tissue perfusion in the living organism.

The present invention is particularly suited for animal studies. However, the present invention has even greater potential utility for the clinical evaluation of humans when using biodegradable radiopaque microspheres which will biodegrade in a relatively short period of time; for example, one or two hours.

These and various other advantages and features of novelty which characterize the present invention are pointed out with particularity in the claims annexed to and forming a part hereof. However, for a better understanding of the invention, its advantages and objects obtained by its use, reference should be had to the drawings which form a further part hereof and to the accompanying descriptive matter in which there is illustrated and described several embodiments of the present invention.

BRIEF DESCRIPTION OF THE DRAWINGS

In the drawings, in which like reference numerals and letters indicate corresponding parts throughout the several views;

FIG. 1 is an overall system diagram of an embodiment in accordance with the principles of the present invention;

FIG. 2 is a diagrammatic view of arterial catherization of a peripheral artery for delivery of a suspension of radiopaque microspheres to the left main coronary artery of the heart; and FIG. 3 is a diagrammatic view illustrating three regions of interest in a hypothetical CT scan wherein radiopaque microspheres have been delivered to the heart as illustrated in FIG. 2.

DETAILED DESCRIPTION OF AN EMBODIMENT OF THE INVENTION

Diagrammatically illustrated in FIG. 1 is an embodiment of an imaging system and method using radiopaque microspheres in accordance with the principles of the present invention, the embodiment being generally referenced by the reference numeral 20. As illustrated, radiopaque microspheres are administered selectively or systemically to organ tissue 22. A conventional computerized tomography (CT) scanner 24 then scans the organ tissue 22 with X-rays and provides a visual CT image 26 and/or a statistical report 28 with numerical CT numbers over specified regions of interest. More particularly, an embodiment in accordance with the principles of the present invention for measuring myocardial tissue perfusion in dogs will now be described although it will be appreciated that the present invention has application for measurement of any organ tissue perfusion as well as disbursement of blood throughout the bodies of both humans and animals.

Diagrammatically illustrated in FIG. 2 is the selective delivery of radiopaque microspheres to the left main coronary artery of the heart via a peripheral arteriol catherization, such as through the femoral artery. In this embodiment, a suspension of pure 15–18 micron tungsten microspheres is delivered to the left main coronary artery by conventional arterial catherization techniques. In this embodiment the tungsten microspheres have weight densities of approximately 19.35 grams per cubic centimeter. The suspension used might include 5 cc of 10 percent Dextran solution and three drops of 5 percent Tween 80 solution, which are mechanically and ultrasonically agitated with the tungsten microspheres. Multiple dosages of the suspension are delivered from a syringe 30 attached to an outer catheter 32 which terminates in the left main coronary artery. Typically, two or three dosages spaced over one or two minutes might be delivered so as to provide a total delivery of three million tungsten microspheres into the left main coronary artery. Also illustrated in this particular embodiment is an inner catheter 34 which extends into the left anterior descending (LAD) coronary artery and is used for delivery of an adenosine solution to provide drug induced vasodilation of the left anterior descending (LAD) coronary artery. This enables the left anterior descending (LAD) coronary artery to circumflex (CX) coronary artery flow ratios to be evaluated after selective left anterior descending (LAD) adenosine induced vasodilation.

After radiopaque microsphere injections are completed, the isolated or in situ organs are scanned in a conventional CT scanner. Conventional CT operating parameters are utilized. Relative CT numbers are then calculated over uniform regions of interest according to the following equation:

$$CT\# = a \times \left[ \frac{u\text{material} - u\text{H}_2\text{O}}{u\text{H}_2\text{O}} \right]$$

Where a is a scaling factor=1000, and $u\text{H}_2\text{O}$ and umaterial are the linear attenuation coefficients of water and the tungsten, respectively.

In this embodiment, CT numbers are obtained for uniform regions of interest over the control nonradiopaque microsphere perfused right ventricle (RV) region, over the left anterior descending (LAD) coronary artery region, and over the circumflex (CX) coronary artery region. A hypothetical visual CT image of these three regions of interest is illustrated in FIG. 3 wherein A is the LAD distribution, B is the circumflex (CX) distribution, and C is the right ventricular distribution.

Once the CT numbers for the three regions of interest (A, B, C) are obtained, the relative flow distribution ratio between the LAD region of interest (A) and the CX region of interest (B) can be calculated as follows:

$$\frac{LAD\ CT\# - RV\ CT\#}{CX\ CT\# - RV\ CT\#}$$

The right ventricular (RV) region of interest serves as a base-line control since no radiopaque microspheres were delivered to the right ventricle.

In the above described embodiment, nonradioactive nonbiodegradable stable tungsten microspheres were utilized. However, in clinical evaluation of humans, biodegradable radiopaque microspheres, for example, an albumin molecule either containing or complexed with a radiopaque substance, will preferably be utilized. Additionally, it will be appreciated that other forms and compositions of both biodegradable and nonbiodegradable radiopaque microspheres might be utilized in keeping with the principles of the present invention.

Furthermore, as previously indicated, the present invention might be utilized to evaluate tissue perfusion of any organ in the body and/or at any location throughout the body. Additionally, administration of the radiopaque microsphere might be accomplished selectively or systemically.

When utilizing the radiopaque microspheres of the present invention with the human heart, it might be necessary to utilize a "fast" CT scanner because of the rapidity of motion of the beating heart. This is not a problem with other organs, such as the kidney, lungs, liver, etc., which are relatively motionless and stable. When evaluating animal hearts, transient vagal nerve stimulation can be utilized to temporarily stop the beating heart for a sufficient amount of time to enable a CT scan with a conventional "slower" CT scanner.

Additionally, although the radiopaque microspheres of the embodiment described are opaque to X-rays, it will be appreciated that the microspheres might be opaque with respect to other forms of electromagnetic radiation. Furthermore, the microspheres might be capable of being visualized and/or exhibiting identifiable characteristics when exposed to other forms of imaging or detection techniques, including nuclear magnetic resonance (NMR) or ultra sound.

It is to be understood that even though numerous characteristics and advantages of the invention have been set forth in the foregoing description, together with details of the structure and function of the invention, the disclosure is illustrative only, and changes may be made in detail, especially in matters of shape, size and arrangement of parts, within the principle of the invention, to the full extent indicated by the broad general meaning of the terms in which the appended claims are expressed.

What is claimed is:

1. An imaging method for evaluating organ tissue perfusion, comprising the steps of:
   (a) administering radiopaque microspheres to the organ tissue which become occluded in terminal capillary beds in the organ tissue;
   (b) subjecting the organ tissue to electromagnetic radiation; and
   (c) measuring the electromagnetic radiation from selected regions of interest in the organ tissue, thereby quantitating the organ tissue perfusion in the selected regions of interest.

2. A method in accordance with claim 1, including the step of comparing the amount of electromagnetic radiation detected over selected regions of interest in the organ tissue.

3. A method in accordance with claim 1, wherein the radiopaque microspheres are biodegradable.

4. A method in accordance with claim 1, including the step of selectively delivering the radiopaque microspheres to the organ tissue.

5. A method in accordance with claim 1, including the step of systemically delivering the radiopaque microspheres to the organ tissue.

6. A method in accordance with claim 1, wherein the radiopaque microspheres are non-radioactive.

7. An imaging method for evaluating organ tissue perfusion, comprising the steps of:
   (a) administering non-radioactive radiopaque microspheres to the organ tissue which become occluded in terminal capillary beds in the organ tissue;
   (b) scanning the organ tissue with a computerized x-ray tomography (CT) scanner device to detect the presence of the radiopaque microspheres in the organ tissue.

8. A method in accordance with claim 7, further including the step of providing a visual CT image.

9. A method in accordance with claim 7, further including the step of calculating a numerical CT value representative of the relative density of the radiopaque microspheres in the organ tissue, whereby the relative tissue perfusion in a selected region of interest can be determined.

10. A method in accordance with claim 7, wherein the microspheres used are biodegradable.

11. A method in accordance with claim 7, wherein the microspheres used are nonbiodegradable.

12. An imaging method for evaluating organ tissue perfusion, comprising the steps of:
   (a) administering non-radioactive, radiopaque microspheres to the organ tissue which become occluded in terminal capillary beds in the organ tissue;
   (b) subjecting the organ tissue to electromagnetic x-ray radiation; and
   (c) measuring the transmission of the electromagnetic x-ray radiation as attentuated by the radiopaque microspheres from selected regions of interest in the organ tissue, thereby quantitating the organ tissue perfusion in the selected regions of interest based on differences in the organ tissue radiopacity.

13. An imaging method in accordance with claim 12, wherein steps (a) and (b) are performed by imaging the organ tissue with a computerized x-ray tomography (CT) scanner device to detect the presence of the radiopaque microspheres in the organ tissue.

14. An imaging method in accordance with claim 13, wherein the radiopaque microspheres have a diameter of 15 to 18 microns.

15. An imaging method in accordance with claim 13, wherein the radiopaque microspheres are comprised of metal.

16. An imaging method in accordance with claim 15, wherein the radiopaque microspheres are comprised of tungsten.

* * * * *